United States Patent
Markovitz (10) Patent No.: US 10,561,325 B2
(45) Date of Patent: Feb. 18, 2020

(54) SYSTEM AND METHOD FOR GENERATING ELECTROPHYSIOLOGY MAPS

(71) Applicant: St. Jude Medical, Cardiology Division, Inc., St. Paul, MN (US)

(72) Inventor: Craig Markovitz, Leipzig (DE)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 258 days.

(21) Appl. No.: 15/783,599

(22) Filed: Oct. 13, 2017

(65) Prior Publication Data

US 2018/0132743 A1 May 17, 2018

Related U.S. Application Data

(60) Provisional application No. 62/420,811, filed on Nov. 11, 2016.

(51) Int. Cl.
| | | |
|---|---|---|
| *A61B 5/04* | (2006.01) | |
| *A61B 5/0402* | (2006.01) | |
| *A61B 5/00* | (2006.01) | |
| *G06F 19/00* | (2018.01) | |
| *A61B 5/042* | (2006.01) | |
| *G16H 50/50* | (2018.01) | |

(52) U.S. Cl.
CPC ........ *A61B 5/04012* (2013.01); *A61B 5/0402* (2013.01); *A61B 5/0422* (2013.01); *A61B 5/7203* (2013.01); *A61B 5/7246* (2013.01); *G16H 50/50* (2018.01); *A61B 5/748* (2013.01)

(58) Field of Classification Search
None
See application file for complete search history.

(56) References Cited

U.S. PATENT DOCUMENTS

| | | | |
|---|---|---|---|
| 5,697,377 | A | 12/1997 | Wittkampf |
| 5,983,126 | A | 11/1999 | Wittkampf |
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |

(Continued)

OTHER PUBLICATIONS

International Search Report and Written Opinion for PCT/US2017/056593, dated Dec. 21, 2017.

*Primary Examiner* — Brian T Gedeon
(74) *Attorney, Agent, or Firm* — Wiley Rein LLP (57) ABSTRACT

A method of generating an electrophysiology map of a portion of a patient's anatomy includes receiving a plurality of electrophysiology data points, each including an associated electrophysiological signal. A template electrophysiology data point and one or more unwanted electrophysiology data points are selected from the plurality of electrophysiology data points. The electrophysiological signal associated with the template electrophysiology data point is defined as a template electrophysiological signal, while the electrophysiological signal(s) associated with the unwanted electrophysiology data point(s) is/are defined as unwanted electrophysiological signal(s). For any given electrophysiology data point, if the morphology of its associated electrophysiological signal is more similar to the morphology of an unwanted electrophysiological signal than to the morphology of the template electrophysiological signal, the given electrophysiology data point is rejected/excluded from an electrophysiology map.

30 Claims, 3 Drawing Sheets

(56) References Cited

U.S. PATENT DOCUMENTS

| | | |
|---|---|---|
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2012/0184858 A1 | 7/2012 | Harlev |
| 2015/0057507 A1 | 2/2015 | Koyrakh et al. |

SYSTEM AND METHOD FOR GENERATING ELECTROPHYSIOLOGY MAPS

CROSS-REFERENCE TO RELATED APPLICATIONS

This application claims the benefit of U.S. provisional application No. 62/420,811, filed 11 Nov. 2016, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for generating an electrophysiology map from data collected by a roving electrophysiology probe.

Electrophysiological mapping, and more particularly electrocardiographic mapping, is a part of numerous cardiac diagnostic and therapeutic procedures. As the complexity of such procedures increases, however, the electrophysiology maps utilized must increase in quality, in density, and in the rapidity and ease with which they can be generated.

BRIEF SUMMARY

Disclosed herein is a method of generating an electrophysiology map of a portion of a patient's anatomy, including: receiving an electrophysiology map including a plurality of electrophysiology data points, each electrophysiology data point including an electrophysiological signal having a signal morphology; defining a template electrophysiological signal having a template morphology; defining an unwanted electrophysiological signal having an unwanted morphology; comparing the signal morphology of an electrophysiological signal of an electrophysiology data point within the electrophysiology map to both the template morphology of the template electrophysiological signal and the unwanted morphology of the unwanted electrophysiological signal; and removing the electrophysiology data point from the electrophysiology map when the signal morphology of the electrophysiological signal of the electrophysiology data point is more similar to the unwanted morphology of the unwanted electrophysiological signal than to the template morphology of the template electrophysiological signal.

According to aspects of the disclosure, the unwanted electrophysiological signal having an unwanted morphology can be defined by: selecting an electrophysiology data point from the electrophysiology map; and defining an electrophysiological signal associated with the selected electrophysiology data point as the unwanted electrophysiological signal. Similarly, the template electrophysiological signal having the template morphology can be defined by: selecting an electrophysiology data point from the electrophysiology map; and defining an electrophysiological signal associated with the selected electrophysiology data point as the template electrophysiological signal.

The steps of comparing the signal morphology of an electrophysiological signal of an electrophysiology data point within the electrophysiology map to both the template morphology of the template electrophysiological signal and the unwanted morphology of the unwanted electrophysiological signal and removing the electrophysiology data point from the electrophysiology map when the signal morphology of the electrophysiological signal of the electrophysiology data point is more similar to the unwanted morphology of the unwanted electrophysiological signal than to the template morphology of the template electrophysiological signal can also be repeated for at least one additional electrophysiology data point within the electrophysiology map.

In embodiments of the disclosure, the method can also include: collecting an additional electrophysiology data point including an electrophysiological signal having a signal morphology; comparing the signal morphology of the electrophysiological signal of the collected additional electrophysiology data point; and adding the collected additional electrophysiology data point to the electrophysiology map when the signal morphology of the electrophysiological signal of the collected additional electrophysiology data point is more similar to the template morphology of the template electrophysiological signal than to the unwanted morphology of the unwanted electrophysiological signal.

In further embodiments, the method can also include: defining an additional unwanted electrophysiological signal having an additional unwanted morphology; comparing the signal morphology of the electrophysiological signal of the electrophysiology data point within the electrophysiology map to both the template morphology of the template electrophysiological signal and the additional unwanted morphology of the additional unwanted electrophysiological signal; and removing the electrophysiology data point from the electrophysiology map when the signal morphology of the electrophysiological signal of the electrophysiology data point is more similar to the additional unwanted morphology of the additional unwanted electrophysiological signal than to the template morphology of the template electrophysiological signal.

Various approaches to comparing the signal morphology of an electrophysiological signal of an electrophysiology data point within the electrophysiology map to both the template morphology of the template electrophysiological signal and the unwanted morphology of the unwanted electrophysiological signal are contemplated. For example, according to some aspects of the disclosure, a first morphology matching score is computed between the signal morphology of the electrophysiological signal of the electrophysiology data point and the template morphology of the template electrophysiological signal; and a second morphology matching score is computed between the signal morphology of the electrophysiological signal of the electrophysiology data point and the unwanted morphology of the unwanted electrophysiological signal. The first morphology matching score can be computed by: computing a template area between the template electrophysiological signal and a zero signal; computing a first distance between the electrophysiological signal of the electrophysiology data point and the template electrophysiological signal; and dividing the first computed distance by the computed template area. Similarly, the second morphology matching score can be computed by: computing an unwanted area between the unwanted electrophysiological signal and the zero signal; computing a second distance between the electrophysiological signal of the electrophysiology data point and the unwanted electrophysiological signal; and dividing the second computed distance by the computed unwanted area.

Alternatively, the first morphology matching score can be computed according to an equation $S_t = P_t * f(r_t)$, where $P_t$ is the Pearson Correlation Coefficient of the template electrophysiological signal and the electrophysiological signal of the electrophysiology data point, $r_t$ is the ratio of amplitudes of the template electrophysiological signal and the electrophysiological signal of the electrophysiology data point and is defined such that $0 \le r_t \le 1$, and $f(r_t)$ is a monotonically increasing function with output $0 \le f(r_t) \le 1$. Likewise, the second morphology matching score can be computed according to an equation $S_u = P_u * f(r_u)$, where $P_u$ is the Pearson Correlation Coefficient of the template electrophysiological signal and the electrophysiological signal of the electrophysiology data point, $r_u$ is the ratio of amplitudes of the template electrophysiological signal and the electrophysiological signal of the electrophysiology data point and is defined such that $0 \le r_u \le 1$, and $f(r_u)$ is a monotonically increasing function with output $0 \le f(r_u) \le 1$.

A graphical representation of the electrophysiology map on a three dimensional model of the portion of the patient's anatomy can be output after the removing step.

Also disclosed herein is a method of generating an electrophysiology map of a portion of a patient's anatomy, including the following steps: receiving an initial set of electrophysiology data points including a plurality of electrophysiology data points, each electrophysiology data point including an associated electrophysiological signal; selecting, from the plurality of electrophysiology data points, a template electrophysiology data point; defining the electrophysiological signal associated with the template electrophysiology data point as a template electrophysiological signal; selecting, from the plurality of electrophysiology data points, an unwanted electrophysiology data point; defining the electrophysiological signal associated with the unwanted electrophysiology data point as an unwanted electrophysiological signal; and for at least one electrophysiology data point of the plurality of electrophysiology data points other than the template electrophysiology data point and the unwanted electrophysiology data point: computing a morphological similarity between the electrophysiological signal of the at least one electrophysiology data point and the template signal; computing a morphological similarity between the electrophysiological signal of the at least one electrophysiology data point and the unwanted signal; and removing the at least one electrophysiology data point from the initial set of electrophysiology data points when the morphological similarity between the electrophysiological signal of the at least one electrophysiology data point and the unwanted signal exceeds the morphological similarity between the electrophysiological signal of the at least one electrophysiology data point and the template signal.

It is also contemplated to select, from the plurality of electrophysiology data points, a plurality of unwanted electrophysiology data points. The plurality of electrophysiological signals associated with the plurality of unwanted data points can be defined as a plurality of unwanted electrophysiological signals. A plurality of morphological similarities can be computed between the electrophysiological signal of the at least one electrophysiology data point and the plurality of unwanted electrophysiological signals. The at least one electrophysiology data point can be removed from the initial set of electrophysiology data points when the morphological similarity between the electrophysiological signal of the at least one electrophysiology data point and the unwanted signal exceeds the morphological similarity between the electrophysiological signal of the at least one electrophysiology data point and the template signal comprises removing the at least one electrophysiology data point from the initial set of electrophysiology data points when any of the plurality of morphological similarities is greater than the morphological similarity between the electrophysiological signal of the at least one electrophysiology data point and the template signal.

In embodiments, the method also includes outputting a graphical representation of the electrophysiology map on a three dimensional model of the portion of the patient's anatomy after the removing step.

The morphological similarity between the electrophysiological signal of the at least one electrophysiology data point and the template signal can be computed as a function of a distance between the electrophysiological signal of the at least one electrophysiology data point and the template signal. Similarly, the morphological similarity between the electrophysiological signal of the at least one electrophysiology data point and the unwanted signal can be computed as a function of a distance between the electrophysiological signal of the at least one electrophysiology data point and the unwanted signal.

In other aspects of the disclosure, the morphological similarity between the electrophysiological signal of the at least one electrophysiology data point and the template signal can be computed as a function of the Pearson Correlation Coefficient between the electrophysiological signal of the at least one electrophysiology data point and the template signal, and the morphological similarity between the electrophysiological signal of the at least one electrophysiology data point and the unwanted signal can be computed as a function of the Pearson Correlation Coefficient between the electrophysiological signal of the at least one electrophysiology data point and the unwanted signal.

It is also contemplated that the method can include: receiving an additional electrophysiology data point including an associated electrophysiological signal; computing a morphological similarity between the electrophysiological signal of the additional electrophysiology data point and the template signal; computing a morphological similarity between the electrophysiological signal of the additional electrophysiology data point and the unwanted signal; and adding the additional electrophysiology data point to the initial set of electrophysiology data points when the morphological similarity between the electrophysiological signal of the at least one electrophysiology data point and the template signal exceeds the morphological similarity between the electrophysiological signal of the at least one electrophysiology data point and the unwanted signal.

The instant disclosure also provides a system for generating an electrophysiology map of a portion of a patient's anatomy. The system includes: a rejection processor configured to: compute a morphological similarity between an electrophysiological signal associated with an electrophysiology data point and a template electrophysiological signal; compute a morphological similarity between the electrophysiological signal associated with the electrophysiology data point and an unwanted electrophysiological signal; and reject the electrophysiology data point from inclusion in an electrophysiology map when the morphological similarity between the electrophysiological signal associated with the electrophysiology data point and an unwanted electrophysiological signal exceeds the morphological similarity between the electrophysiological signal associated with the electrophysiology data point and the template electrophysiological signal. The system can also include a mapping processor configured to generate a graphical representation of the electrophysiology map after rejection of one or more electrophysiology data points by the rejection processor.

The rejection processor can receive as input a plurality of electrophysiology data points, each having an associated electrophysiological signal. It can also receive as input a user's selection of one of the plurality of electrophysiology data points, and can be configured to define the electrophysiological signal associated with the selected one of the plurality of electrophysiology data points as the unwanted electrophysiological signal.

The rejection processor can be configured to compute the morphological similarity between the electrophysiological signal associated with an electrophysiology data point and the template electrophysiological signal as a function of a distance between the electrophysiological signal of the electrophysiology data point and the template electrophysiological signal. Similarly, the rejection processor can be configured to compute the morphological similarity between the electrophysiological signal associated with the electrophysiology data point and the unwanted electrophysiological signal as a function of a distance between the electrophysiological signal of the electrophysiology data point and the unwanted electrophysiological signal.

Alternatively or additionally, the rejection processor can be configured to compute the morphological similarity between the electrophysiological signal associated with an electrophysiology data point and the template electrophysiological signal as a function of the Pearson Correlation Coefficient between the electrophysiological signal of the electrophysiology data point and the template electrophysiological signal and to compute the morphological similarity between the electrophysiological signal associated with the electrophysiology data point and the unwanted electrophysiological signal as a function of the Pearson Correlation Coefficient between the electrophysiological signal of the electrophysiology data point and the unwanted electrophysiological signal.

According to aspects of the disclosure, the rejection processor can be configured to compute a plurality of morphological similarities between the electrophysiological signal associated with the electrophysiology data point and a plurality of unwanted electrophysiological signals. The electrophysiology data point can be rejected from inclusion in the electrophysiology map when the morphological similarity between the electrophysiological signal associated with the electrophysiology data point and any of the plurality of unwanted electrophysiological signals exceeds the morphological similarity between the electrophysiological signal associated with the electrophysiology data point and the template electrophysiological signal.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses and systems for the creation of electrophysiology maps (e.g., electrocardiographic maps). More particularly, the teachings herein relate to the automatic exclusion of unwanted electrophysiology data points from such electrophysiology maps. For example, a physician may wish to eliminate certain electrophysiology data points from an electrophysiology map if the original settings for inclusion of electrophysiology data points were too lax. Likewise, the physician may wish to eliminate certain electrophysiology data points from an electrophysiology map if too few ECG channels were used to determine the beat of interest (referred to herein as a "template beat"), resulting in the collection of incorrectly mapped beats.

For purposes of illustration, several exemplary embodiments will be described in detail herein in the context of a cardiac electrophysiology procedure. It is contemplated, however, that the methods, apparatuses, and systems described herein can be utilized in other contexts.

Figure 1:
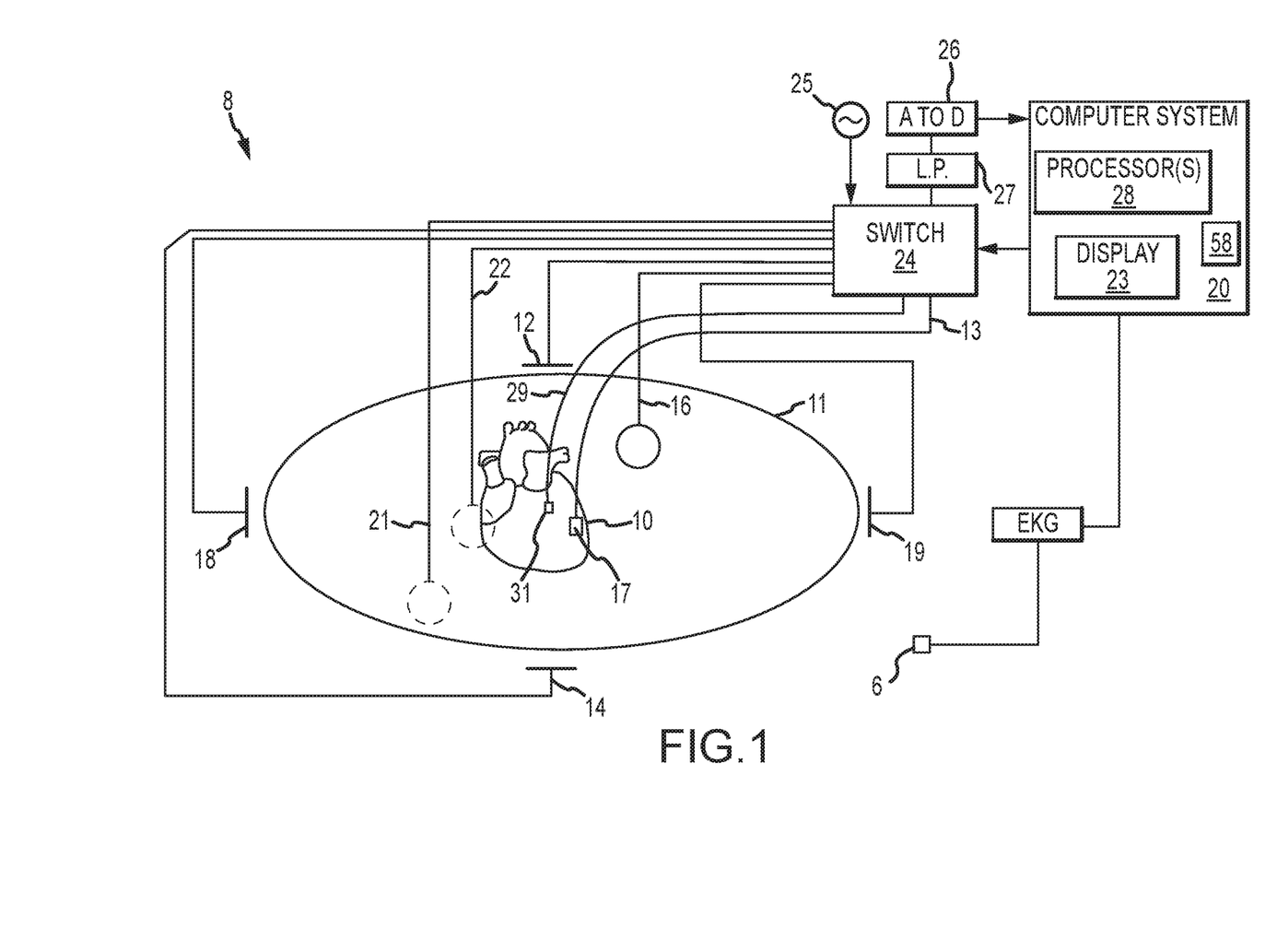
FIG. 1 is a schematic diagram of an electroanatomical mapping system, such as may be used in an electrophysiology study.

FIG. 1 shows a schematic diagram of a system 8, such as an electroanatomical mapping system, for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data (e.g., cardiac electrograms) at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, the leads and their connections to computer system 20 are not illustrated in FIG. 1.

A representative catheter 13 having at least one electrode 17 (e.g., a distal electrode) is also depicted in schematic fashion in FIG. 1. This representative catheter electrode 17 can be referred to as a "measurement electrode" or a "roving electrode." Typically, multiple electrodes on catheter 13, or on multiple such catheters, will be used. In one embodiment, for example, system 8 may utilize sixty-four electrodes on twelve catheters disposed within the heart and/or vasculature of the patient.

In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the Ensite™ Array™ non-contact mapping catheter of St. Jude Medical, Inc., can be utilized.

Figure 2:
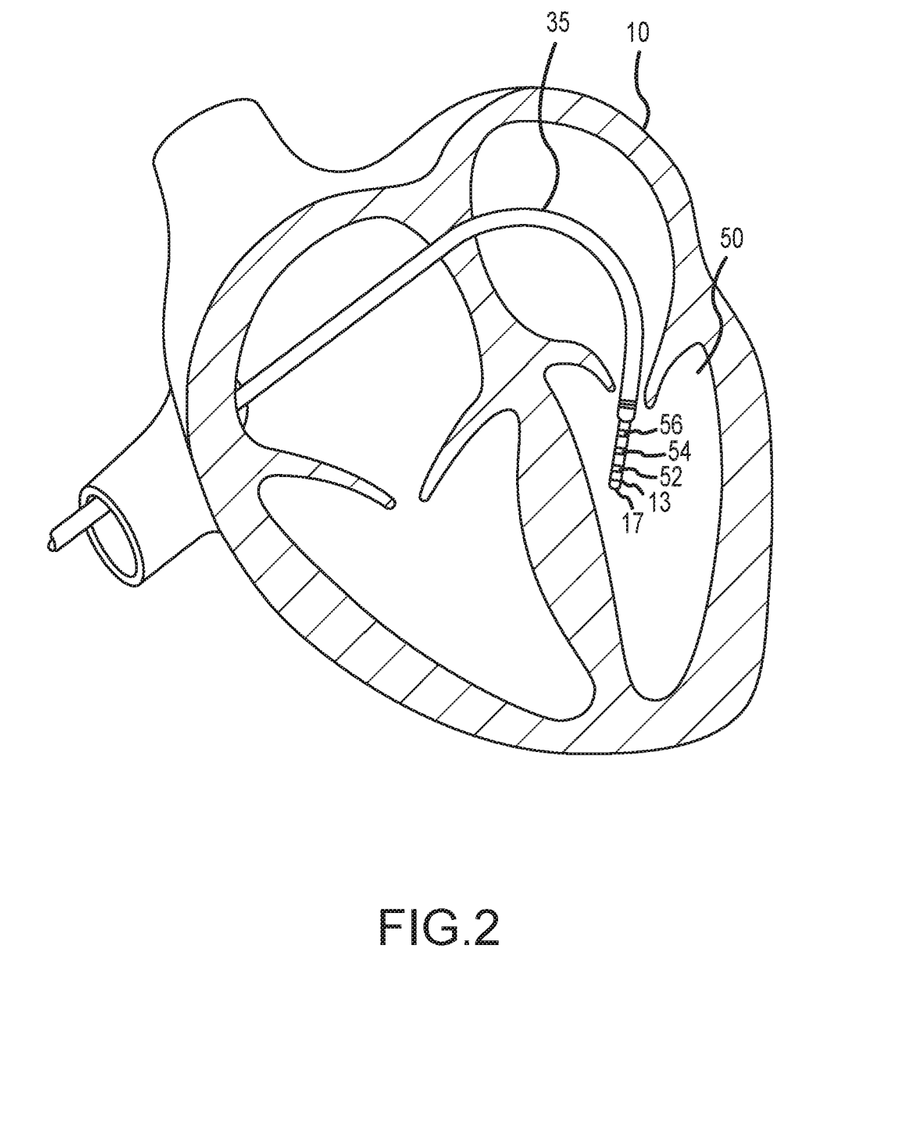
FIG. 2 depicts an exemplary catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the conduction velocity mapping techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another system that relies upon electrical fields. Other systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation System, as well as MediGuide™ Technology and the EnSite™ Precision™ system, both from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Figure 3:
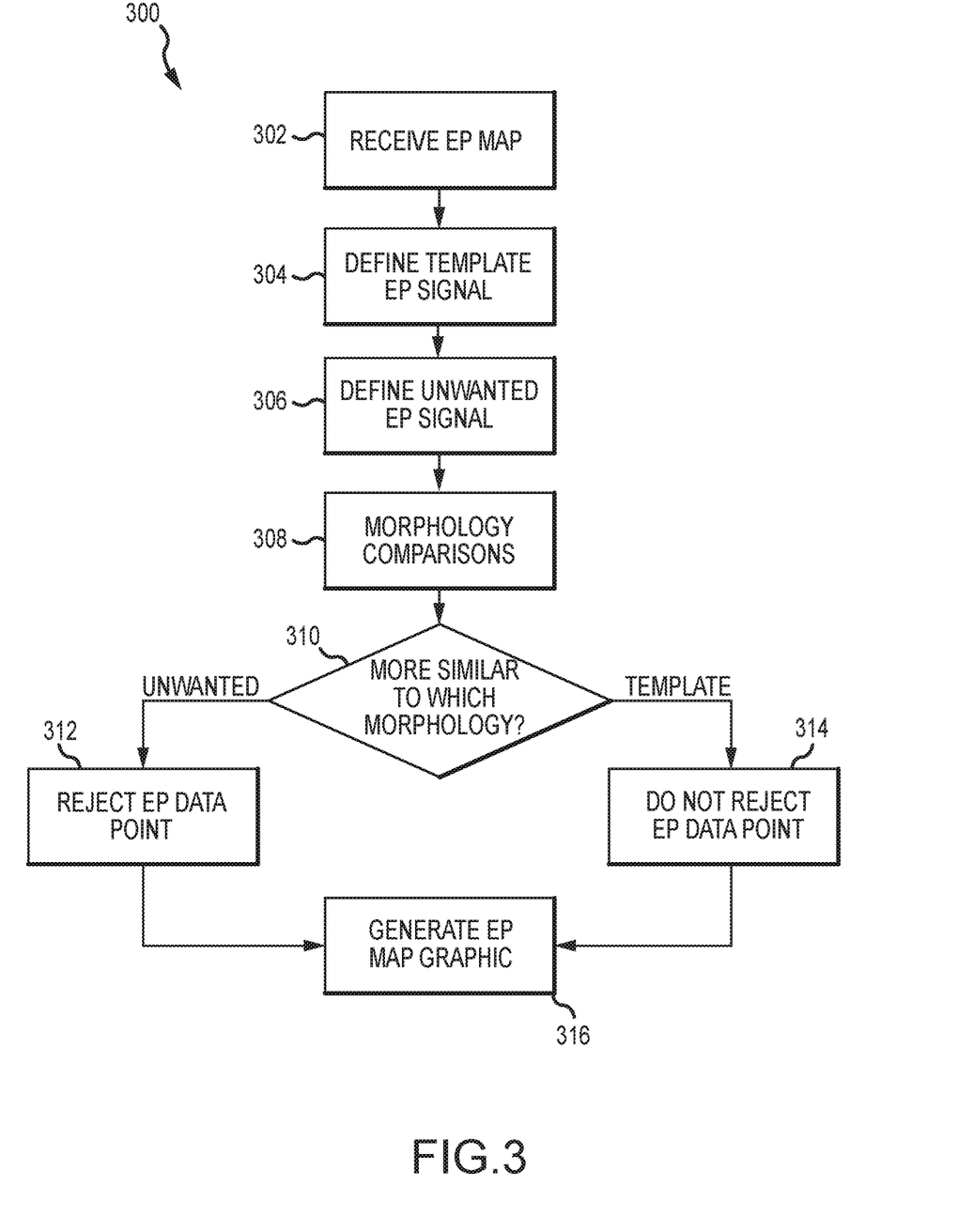
FIG. 3 is a flowchart depicting representative steps that can be followed in a method of generating an electrophysiology map according to an embodiment disclosed herein.

Various aspects of the instant disclosure will now be described with reference to FIG. 3, which is a flowchart depicting representative steps of an exemplary method 300 for generating an electrophysiology map according to the instant disclosure. In some embodiments, for example, FIG. 3 may represent several exemplary steps that can be carried out by the computer 20 of FIG. 1 (e.g., by one or more processors 28 executing one or more specialized modules, such as a rejection module 58 as further described below). It should be understood that the representative steps described below can be software- and/or hardware-implemented, and that they may be executed on a single CPU, which may have one or more threads, or distributed across multiple CPUs, each of which may have one or more threads, in a parallel processing environment. For the sake of explanation, the term "signal processor" is used herein to describe both hardware- and software-based implementations of the teachings herein.

In block 302, an electrophysiology map is received, for example in computer 20. Those of ordinary skill in the art will appreciate that electrophysiology maps include a plurality of electrophysiology data points, and each electrophysiology data point in turn includes both measured electrophysiology data (e.g., an electrophysiological signal, such as a cardiac electrograms ("EGM")) and location data (e.g., information regarding the location of catheter 13 and/or the electrodes 17, 52, 54, 56 thereon), allowing the measured electrophysiology information to be associated with a particular location in space (that is, allowing the measured electrophysiology information to be interpreted as indicative of electrical activity at a point on the patient's heart).

Those of ordinary skill in the art will be familiar with various aspects of electrophysiology maps. By way of example only, however, United States patent application publication no. 2015/0057507, which is hereby incorporated by reference as though fully set forth herein, describes various methods and systems for the creation of electrophysiology maps as to which the teachings of the instant disclosure can be applied.

The electrophysiology map received in block 302 can be a real time map or a map from a previously-conducted electrophysiology study. That is, the teachings herein can be applied both during an ongoing electrophysiology study (e.g., to reject and remove electrophysiology data points that have already been collected and included in an ongoing electrophysiology map and/or to prevent the inclusion of later-collected electrophysiology data points during the same electrophysiology study) and to historical electrophysiology maps (e.g., to refine a previously-generated electrophysiology map by deleting certain electrophysiology data points contained therein, such as may be desirable during post-processing to reduce the required computational overhead).

A template electrophysiological signal is defined in block 304. As used herein, a "template electrophysiological signal" is defined as an electrophysiological signal possessing a morphology (a "template morphology") that is of interest to a practitioner in a particular electrophysiology study. In embodiments of the disclosure, the template electrophysiological signal is defined as the electrophysiological signal corresponding to the first electrophysiology data point added to the electrophysiology map; such electrophysiology data point can, for example, be manually captured in a conventional manner (e.g., by clicking a "freeze and save" button on a graphical user interface).

It is also contemplated, however, that the template electrophysiological signal can be user-selected at a later point in the process, either initially or as a replacement for a previously-defined template electrophysiological signal. For example, the user can be allowed to select, such as by pointing and clicking on a graphical representation of an electrophysiology map, an electrophysiological data point that possesses the electrophysiological signal of interest. Once the user has selected an electrophysiology data point in this (or any other) manner, the electrophysiological signal associated therewith can be defined (or re-defined, as applicable) as the template electrophysiological signal.

Similarly, an unwanted electrophysiological signal is defined in block 306. As used herein, an "unwanted electrophysiological signal" is defined as an electrophysiological signal possessing a morphology (an "unwanted morphology") that is not of interest to a practitioner in a particular electrophysiology study. According to aspects of the disclosure, the unwanted electrophysiological signal can be user-selected in a manner analogous to that described above with respect to user-selected template electrophysiological signals.

Morphology comparisons are carried out in block 308 and decision block 310. In particular, for a given electrophysiology data point within the electrophysiology map, the morphology of the electrophysiological signal associated therewith (the "signal morphology") is compared to both the template morphology of the template electrophysiological signal and the unwanted morphology of the unwanted electrophysiological signal.

If, in decision block 310, the signal morphology is more similar to the unwanted morphology than to the template morphology, then the given electrophysiology data point is rejected from the electrophysiology map in block 312.

If, on the other hand, the signal morphology is more similar to the template morphology than to the unwanted morphology, then the given electrophysiology data point is not rejected from/remains included in the electrophysiology map in block 314.

Various techniques for computing morphological similarities in block 308, for purpose of carrying out morphology comparisons in block 310, are regarded as within the scope of the instant disclosure. These techniques generally include computing matching scores between the signal morphology of the electrophysiological signal associated with the given electrophysiology data point, on the one hand, and either the template morphology of the template electrophysiological signal or the unwanted morphology of the unwanted electrophysiological signal, on the other hand. A higher matching score indicates a higher degree of similarity.

Several approaches to computing matching scores are described in United States patent application publication no. 2015/0057507, which is incorporated by reference above. For the sake of convenience of the reader, however, certain of these techniques are also expressly described below.

In one aspect, a matching score can be calculated as follows. First, a distance can be computed between the template electrophysiological signal or the unwanted electrophysiological signal, on the one hand, and a zero signal, on the other hand. This distance is referred herein to as a "template area" if computed relative to the template electrophysiological signal and as an "unwanted area" if computed relative to the unwanted electrophysiological signal.

Next, a distance is computed between the electrophysiological signal associated with the given electrophysiology data point, on the one hand, and the template electrophysiological signal or the unwanted electrophysiological signal, on the other hand. This distance can then be divided by the respective area (e.g., the template area or the unwanted area). The resulting ratio can be subtracted from one and expressed as a percentage matching score; if the ratio is greater than one, a 0% matching score is assigned. A higher matching score corresponds to a higher degree of similarity between two morphologies.

In other embodiments of the disclosure, the Pearson Correlation Coefficient can be used as an alternative or in addition to a distance function in order to compute a morphology matching score. For example, a score S can be computed according to the equation $S=P*f(r)$, where: (1) P is the Pearson Correlation Coefficient of either the template electrophysiological signal or the unwanted electrophysiological signal, on the one hand, and the electrophysiological signal associated with the given electrophysiology data point, on the other hand; (2) r is the ratio of amplitudes of the template electrophysiological signal or the unwanted electrophysiological signal, on the one hand, and the electrophysiological signal associated with the given electrophysiology data point, on the other hand and is defined such that $0 \leq r \leq 1$ (e.g., the larger amplitude is in the denominator when computing r); and (3) f(r) is a monotonically increasing function with output in the range $0 \leq f(r) \leq 1$. Signal amplitudes can be measured by, for example, the standard deviation or peak-to-peak measurement. Further, for purposes of this disclosure, the foregoing variables are presented with a subscript t when referring to a template electrophysiological signal and with a subscript u when referring to an unwanted electrophysiological signal.

The teachings above, which are described with respect to a single given electrophysiology data point from the electrophysiology map and a single user-selected unwanted electrophysiological signal, can be extended in various ways. For example, it is contemplated that the teachings above can be applied to at least one additional given electrophysiology data point within the electrophysiology map; indeed, according to aspects of the disclosure, all of the other electrophysiology data points within the electrophysiology map (e.g., other than the electrophysiology data point(s) that is/are user-selected when defining the unwanted electrophysiological signal(s) and/or the template electrophysiological signal) can be so processed.

As another extension of the foregoing teachings, a user can select multiple unwanted electrophysiology signals, rather than only a single unwanted electrophysiology signal. Where multiple unwanted electrophysiological signals are selected, a given electrophysiology data point can be rejected from the electrophysiology map if it has a signal morphology that is more similar to any of the unwanted morphologies than to the template morphology.

As still another extension, the teachings herein can be applied not only to previously-collected electrophysiology data points, but also to additional electrophysiology data points collected at later times during an electrophysiology study.

In block 316, following the rejection and/or non-rejection of electrophysiology data points in blocks 312 and 314, respectively, a graphical representation of the electrophysiology map can be output, for example on a three dimensional cardiac geometry model.

Although several embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating an electrophysiology map of a portion of a patient's anatomy, comprising:
   receiving an electrophysiology map comprising a plurality of electrophysiology data points, each electrophysiology data point including an electrophysiological signal having a signal morphology;
   defining a template electrophysiological signal having a template morphology;
   defining an unwanted electrophysiological signal having an unwanted morphology;
   comparing the signal morphology of an electrophysiological signal of an electrophysiology data point within the electrophysiology map to both the template morphology of the template electrophysiological signal and the unwanted morphology of the unwanted electrophysiological signal; and
   removing the electrophysiology data point from the electrophysiology map when the signal morphology of the electrophysiological signal of the electrophysiology data point is more similar to the unwanted morphology of the unwanted electrophysiological signal than to the template morphology of the template electrophysiological signal.

2. The method according to claim 1, wherein defining an unwanted electrophysiological signal having an unwanted morphology comprises:
   selecting an electrophysiology data point from the electrophysiology map; and
   defining an electrophysiological signal associated with the selected electrophysiology data point as the unwanted electrophysiological signal.

3. The method according to claim 1, wherein defining a template electrophysiological signal having a template morphology comprises:
   selecting an electrophysiology data point from the electrophysiology map; and
   defining an electrophysiological signal associated with the selected electrophysiology data point as the template electrophysiological signal.

4. The method according to claim 1, further comprising repeating the steps:
   comparing the signal morphology of an electrophysiological signal of an electrophysiology data point within the electrophysiology map to both the template morphology of the template electrophysiological signal and the unwanted morphology of the unwanted electrophysiological signal; and
   removing the electrophysiology data point from the electrophysiology map when the signal morphology of the electrophysiological signal of the electrophysiology data point is more similar to the unwanted morphology of the unwanted electrophysiological signal than to the template morphology of the template electrophysiological signal,
   for at least one additional electrophysiology data point within the electrophysiology map.

5. The method according to claim 1, further comprising:
   collecting an additional electrophysiology data point including an electrophysiological signal having a signal morphology;
   comparing the signal morphology of the electrophysiological signal of the collected additional electrophysiology data point; and
   adding the collected additional electrophysiology data point to the electrophysiology map when the signal morphology of the electrophysiological signal of the collected additional electrophysiology data point is more similar to the template morphology of the template electrophysiological signal than to the unwanted morphology of the unwanted electrophysiological signal.

6. The method according to claim 1, further comprising:
   defining an additional unwanted electrophysiological signal having an additional unwanted morphology;
   comparing the signal morphology of the electrophysiological signal of the electrophysiology data point within the electrophysiology map to both the template morphology of the template electrophysiological signal and the additional unwanted morphology of the additional unwanted electrophysiological signal; and
   removing the electrophysiology data point from the electrophysiology map when the signal morphology of the electrophysiological signal of the electrophysiology data point is more similar to the additional unwanted morphology of the additional unwanted electrophysiological signal than to the template morphology of the template electrophysiological signal.

7. The method according to claim 1, wherein comparing the signal morphology of an electrophysiological signal of an electrophysiology data point within the electrophysiology map to both the template morphology of the template electrophysiological signal and the unwanted morphology of the unwanted electrophysiological signal comprises:
   computing a first morphology matching score between the signal morphology of the electrophysiological signal of the electrophysiology data point and the template morphology of the template electrophysiological signal; and
   computing a second morphology matching score between the signal morphology of the electrophysiological signal of the electrophysiology data point and the unwanted morphology of the unwanted electrophysiological signal.

8. The method according to claim 7, wherein:
   computing a first morphology matching score between the signal morphology of the electrophysiological signal of the electrophysiology data point and the template morphology of the template electrophysiological signal comprises:
      computing a template area between the template electrophysiological signal and a zero signal;
      computing a first distance between the electrophysiological signal of the electrophysiology data point and the template electrophysiological signal; and
      dividing the first computed distance by the computed template area; and
   computing a second morphology matching score between the signal morphology of the electrophysiological signal of the electrophysiology data point and the unwanted morphology of the unwanted electrophysiological signal comprises:
      computing an unwanted area between the unwanted electrophysiological signal and the zero signal;
      computing a second distance between the electrophysiological signal of the electrophysiology data point and the unwanted electrophysiological signal; and
      dividing the second computed distance by the computed unwanted area.

9. The method according to claim 7, wherein:
computing a first morphology matching score between the signal morphology of the electrophysiological signal of the electrophysiology data point and the template morphology of the template electrophysiological signal comprises computing the first morphology matching score according to an equation $S_t = P_t * f(r_t)$, where $P_t$ is the Pearson Correlation Coefficient of the template electrophysiological signal and the electrophysiological signal of the electrophysiology data point, $r_t$ is the ratio of amplitudes of the template electrophysiological signal and the electrophysiological signal of the electrophysiology data point and is defined such that $0 \leq r_t \leq 1$, and $f(r_t)$ is a monotonically increasing function with output $0 \leq f(r_t) \leq 1$; and computing a second morphology matching score between the signal morphology of the electrophysiological signal of the electrophysiology data point and the unwanted morphology of the unwanted electrophysiological signal comprises computing the unwanted morphology matching score according to an equation $S_u = P_u * f(r_u)$, where $P_u$ is the Pearson Correlation Coefficient of the template electrophysiological signal and the electrophysiological signal of the electrophysiology data point, $r_u$ is the ratio of amplitudes of the template electrophysiological signal and the electrophysiological signal of the electrophysiology data point and is defined such that $0 \leq r_u \leq 1$, and $f(r_u)$ is a monotonically increasing function with output $0 \leq f(r_u) \leq 1$.

10. The method according to claim 1, further comprising outputting a graphical representation of the electrophysiology map on a three dimensional model of the portion of the patient's anatomy after the removing step.

11. A method of generating an electrophysiology map of a portion of a patient's anatomy, comprising:
receiving an initial set of electrophysiology data points comprising a plurality of electrophysiology data points, each electrophysiology data point including an associated electrophysiological signal;
selecting, from the plurality of electrophysiology data points, a template electrophysiology data point;
defining the electrophysiological signal associated with the template electrophysiology data point as a template electrophysiological signal;
selecting, from the plurality of electrophysiology data points, an unwanted electrophysiology data point;
defining the electrophysiological signal associated with the unwanted electrophysiology data point as an unwanted electrophysiological signal; and
for at least one electrophysiology data point of the plurality of electrophysiology data points other than the template electrophysiology data point and the unwanted electrophysiology data point:
computing a morphological similarity between the electrophysiological signal of the at least one electrophysiology data point and the template signal;
computing a morphological similarity between the electrophysiological signal of the at least one electrophysiology data point and the unwanted signal; and
removing the at least one electrophysiology data point from the initial set of electrophysiology data points when the morphological similarity between the electrophysiological signal of the at least one electrophysiology data point and the unwanted signal exceeds the morphological similarity between the electrophysiological signal of the at least one electrophysiology data point and the template signal.

12. The method according to claim 11, wherein:
selecting, from the plurality of electrophysiology data points, an unwanted electrophysiology data point comprises selecting, from the plurality of electrophysiology data points, a plurality of unwanted electrophysiology data points;
defining the electrophysiological signal associated with the unwanted electrophysiology data point as an unwanted electrophysiological signal comprises defining the plurality of electrophysiological signals associated with the plurality of unwanted data points as a plurality of unwanted electrophysiological signals;
computing a morphological similarity between the electrophysiological signal of the at least one electrophysiology data point and the unwanted signal comprises computing a plurality of morphological similarities between the electrophysiological signal of the at least one electrophysiology data point and the plurality of unwanted electrophysiological signals; and
removing the at least one electrophysiology data point from the initial set of electrophysiology data points when the morphological similarity between the electrophysiological signal of the at least one electrophysiology data point and the unwanted signal exceeds the morphological similarity between the electrophysiological signal of the at least one electrophysiology data point and the template signal comprises removing the at least one electrophysiology data point from the initial set of electrophysiology data points when any of the plurality of morphological similarities is greater than the morphological similarity between the electrophysiological signal of the at least one electrophysiology data point and the template signal.

13. The method according to claim 11, further comprising outputting a graphical representation of the electrophysiology map on a three dimensional model of the portion of the patient's anatomy after the removing step.

14. The method according to claim 11, wherein:
the morphological similarity between the electrophysiological signal of the at least one electrophysiology data point and the template signal is computed as a function of a distance between the electrophysiological signal of the at least one electrophysiology data point and the template signal; and
the morphological similarity between the electrophysiological signal of the at least one electrophysiology data point and the unwanted signal is computed as a function of a distance between the electrophysiological signal of the at least one electrophysiology data point and the unwanted signal.

15. The method according to claim 11, wherein:
the morphological similarity between the electrophysiological signal of the at least one electrophysiology data point and the template signal is computed as a function of the Pearson Correlation Coefficient between the electrophysiological signal of the at least one electrophysiology data point and the template signal; and
the morphological similarity between the electrophysiological signal of the at least one electrophysiology data point and the unwanted signal is computed as a function of the Pearson Correlation Coefficient between the electrophysiological signal of the at least one electrophysiology data point and the unwanted signal.

16. The method according to claim 11, further comprising:
receiving an additional electrophysiology data point including an associated electrophysiological signal;

computing a morphological similarity between the electrophysiological signal of the additional electrophysiology data point and the template signal;

computing a morphological similarity between the electrophysiological signal of the additional electrophysiology data point and the unwanted signal; and adding the additional electrophysiology data point to the initial set of electrophysiology data points when the morphological similarity between the electrophysiological signal of the at least one electrophysiology data point and the template signal exceeds the morphological similarity between the electrophysiological signal of the at least one electrophysiology data point and the unwanted signal.

17. A system for generating an electrophysiology map of a portion of a patient's anatomy, comprising:

a rejection processor configured to:

compute a morphological similarity between an electrophysiological signal associated with an electrophysiology data point and a template electrophysiological signal;

compute a morphological similarity between the electrophysiological signal associated with the electrophysiology data point and an unwanted electrophysiological signal; and reject the electrophysiology data point from inclusion in an electrophysiology map when the morphological similarity between the electrophysiological signal associated with the electrophysiology data point and an unwanted electrophysiological signal exceeds the morphological similarity between the electrophysiological signal associated with the electrophysiology data point and the template electrophysiological signal.

18. The system according to claim 17, further comprising a mapping processor configured to generate a graphical representation of the electrophysiology map after rejection of one or more electrophysiology data points by the rejection processor.

19. The system according to claim 17, wherein the rejection processor receives as input a plurality of electrophysiology data points, each having an associated electrophysiological signal.

20. The system according to claim 19, wherein the rejection processor receives as input a user's selection of one of the plurality of electrophysiology data points, and wherein the rejection processor is further configured to define the electrophysiological signal associated with the selected one of the plurality of electrophysiology data points as the unwanted electrophysiology signal.

21. The system according to claim 19, wherein the rejection processor receives as input a user's selection of one of the plurality of electrophysiology data points, and wherein the rejection processor is further configured to define the electrophysiological signal associated with the selected one of the plurality of electrophysiology data points as the template electrophysiological signal.

22. The system according to claim 17, wherein the rejection processor is configured to compute the morphological similarity between the electrophysiological signal associated with an electrophysiology data point and the template electrophysiological signal as a function of a distance between the electrophysiological signal of the electrophysiology data point and the template electrophysiological signal.

23. The system according to claim 22, wherein the rejection processor is further configured to compute the morphological similarity between the electrophysiological signal associated with an electrophysiology data point and the template electrophysiological signal as a function of a template area between the template electrophysiological signal and a zero signal.

24. The system according to claim 17, wherein the rejection processor is configured to compute the morphological similarity between the electrophysiological signal associated with the electrophysiology data point and the unwanted electrophysiological signal as a function of a distance between the electrophysiological signal of the electrophysiology data point and the unwanted electrophysiological signal.

25. The system according to claim 24, wherein the rejection processor is further configured to compute the morphological similarity between the electrophysiological signal associated with an electrophysiology data point and the unwanted electrophysiological signal as a function of an unwanted area between the unwanted electrophysiological signal and a zero signal.

26. The system according to claim 17, wherein the rejection processor is configured to compute the morphological similarity between the electrophysiological signal associated with an electrophysiology data point and the template electrophysiological signal as a function of the Pearson Correlation Coefficient between the electrophysiological signal of the electrophysiology data point and the template electrophysiological signal.

27. The system according to claim 17, wherein the rejection processor is configured to compute the morphological similarity between the electrophysiological signal associated with the electrophysiology data point and the unwanted electrophysiological signal as a function of the Pearson Correlation Coefficient between the electrophysiological signal of the electrophysiology data point and the unwanted electrophysiological signal.

28. The system according to claim 17, wherein the rejection processor is configured to:

compute a plurality of morphological similarities between the electrophysiological signal associated with the electrophysiology data point and a plurality of unwanted electrophysiological signals; and reject the electrophysiology data point from inclusion in the electrophysiology map when the morphological similarity between the electrophysiological signal associated with the electrophysiology data point and any of the plurality of unwanted electrophysiological signals exceeds the morphological similarity between the electrophysiological signal associated with the electrophysiology data point and the template electrophysiological signal.

29. The system according to claim 28, wherein the rejection processor is further configured to include the electrophysiology data point in the electrophysiology map when the morphological similarity between the electrophysiological signal associated with the electrophysiology data point and the template electrophysiological signal exceeds each morphological similarity between the electrophysiological signal associated with the electrophysiology data point and a respective unwanted electrophysiological signal of the plurality of unwanted electrophysiological signals.

30. The system according to claim 17, wherein the rejection processor is further configured to include the electrophysiology data point in the electrophysiology map when the morphological similarity between the electrophysiological signal associated with the electrophysiology data point and the template electrophysiological signal exceeds the morphological similarity between the electrophysiological signal associated with the electrophysiology data point and the unwanted electrophysiological signal.

* * * * *